United States Patent
Lim et al.

(10) Patent No.: US 9,241,827 B2
(45) Date of Patent: Jan. 26, 2016

(54) INTRAVASCULAR HEAT EXCHANGE CATHETER WITH MULTIPLE SPACED APART DISCRETE COOLANT LOOPS

(71) Applicant: Zoll Circulation, Inc., Sunnyvale, CA (US)

(72) Inventors: Alex L. Lim, Santa Clara, CA (US); Masouneh Mafi, Mountain View, CA (US); Venkata Vishnu Gurukula, Mountain View, CA (US)

(73) Assignee: Zoll Circulation, Inc., San Jose, CA (US)

( * ) Notice: Subject to any disclaimer, the term of this patent is extended or adjusted under 35 U.S.C. 154(b) by 198 days.

(21) Appl. No.: 13/653,648

(22) Filed: Oct. 17, 2012

(65) Prior Publication Data
US 2014/0094880 A1    Apr. 3, 2014

Related U.S. Application Data

(60) Provisional application No. 61/707,107, filed on Sep. 28, 2012.

(51) Int. Cl.
  *A61F 7/12*   (2006.01)
  *A61M 25/10*  (2013.01)
  *A61F 7/00*   (2006.01)

(52) U.S. Cl.
  CPC ......... *A61F 7/123* (2013.01); *A61F 2007/0054* (2013.01); *A61F 2007/126* (2013.01)

(58) Field of Classification Search
  CPC ...... A61F 7/12; A61F 7/123; A61F 2007/126
  USPC .................................................. 607/104–106
  See application file for complete search history.

(56) References Cited

U.S. PATENT DOCUMENTS

| | | | |
|---|---|---|---|
| 1,459,112 A | 6/1923 | Mehl |
| 1,857,031 A | 5/1932 | Schaffer |
| 2,663,030 A | 12/1953 | Dahlberg |
| 2,673,987 A | 4/1954 | Upshaw et al. |
| 3,225,191 A | 12/1965 | Calhoun |
| 3,369,549 A | 2/1968 | Armao |
| 3,425,419 A | 2/1969 | Dato |

(Continued)

FOREIGN PATENT DOCUMENTS

| DE | 19531935 | 2/1997 |
|---|---|---|
| GB | 2040169 | 8/1980 |

(Continued)

OTHER PUBLICATIONS

F.W. Behmann, E. Bontke, "Die Regelung der Wärmebildung bei künstlicher Hypothermie", Pflügers Archiv, Bd. 266, S. 408-421 (1958).

(Continued)

*Primary Examiner* — Linda Dvorak
*Assistant Examiner* — Yasamin Ekrami
(74) *Attorney, Agent, or Firm* — John L. Rogitz

(57) ABSTRACT

A catheter has a series of hollow loops arranged along a tube for carrying working fluid from a heat exchange system to exchange heat with a patient in whom the catheter is advanced. The loops when inflated are transverse to the catheter axis and parallel to each other, and circumscribe a hollow passageway through which blood can flow. Blood also flows around the outer perimeters of the loops.

16 Claims, 2 Drawing Sheets

(56) References Cited

U.S. PATENT DOCUMENTS

| | | | | |
|---|---|---|---|---|
| 3,504,674 | A | 4/1970 | Swenson | |
| 3,726,269 | A | 4/1973 | Webster, Jr. | |
| 3,744,555 | A | 7/1973 | Fletcher et al. | |
| 3,751,077 | A | 8/1973 | Hiszpanski | |
| 3,937,224 | A | 2/1976 | Uecker | |
| 3,945,063 | A | 3/1976 | Matsuura | |
| 4,038,519 | A | 7/1977 | Foucras | |
| 4,065,264 | A | 12/1977 | Lewin | |
| 4,103,511 | A | 8/1978 | Kress et al. | |
| 4,126,132 | A | 11/1978 | Portner et al. | |
| 4,153,048 | A | 5/1979 | Magrini | |
| 4,173,228 | A | 11/1979 | Van Steenwyk et al. | |
| 4,181,132 | A | 1/1980 | Parks | |
| 4,298,006 | A | 11/1981 | Parks | |
| 4,459,468 | A | 7/1984 | Bailey | |
| 4,532,414 | A | 7/1985 | Shah et al. | |
| 4,554,793 | A | 11/1985 | Harding, Jr. | |
| 4,581,017 | A | 4/1986 | Sahota | |
| 4,638,436 | A | 1/1987 | Badger et al. | |
| 4,653,987 | A | 3/1987 | Tsuji et al. | |
| 4,661,094 | A | 4/1987 | Simpson | |
| 4,665,391 | A | 5/1987 | Spani | |
| 4,672,962 | A | 6/1987 | Hershenson | |
| 4,754,752 | A | 7/1988 | Ginsburg et al. | |
| 4,787,388 | A | 11/1988 | Hofmann | |
| 4,813,855 | A | 3/1989 | Leveen et al. | |
| 4,849,196 | A | 7/1989 | Yamada et al. | |
| 4,852,567 | A | 8/1989 | Sinofsky | |
| 4,860,744 | A | 8/1989 | Johnson et al. | |
| 4,906,237 | A | 3/1990 | Johansson et al. | |
| 4,941,475 | A | 7/1990 | Williams et al. | |
| 5,037,392 | A * | 8/1991 | Hillstead | 606/194 |
| 5,092,841 | A | 3/1992 | Spears | |
| 5,103,360 | A | 4/1992 | Maeda | |
| 5,106,360 | A | 4/1992 | Ishiwara et al. | |
| 5,192,274 | A | 3/1993 | Bierman | |
| 5,195,965 | A | 3/1993 | Shantha | |
| 5,211,631 | A | 5/1993 | Sheaff | |
| 5,269,758 | A | 12/1993 | Taheri | |
| 5,281,215 | A | 1/1994 | Milder | |
| 5,304,214 | A | 4/1994 | DeFord et al. | |
| 5,342,301 | A | 8/1994 | Saab | |
| 5,344,436 | A | 9/1994 | Fontenot et al. | |
| 5,370,675 | A | 12/1994 | Edwards et al. | |
| 5,383,856 | A | 1/1995 | Bersin | |
| 5,403,281 | A | 4/1995 | O'Neill et al. | |
| 5,433,740 | A | 7/1995 | Yamaguchi | |
| 5,437,673 | A | 8/1995 | Baust et al. | |
| 5,458,639 | A | 10/1995 | Tsukashima et al. | |
| 5,466,208 | A | 1/1996 | Ginsburg | |
| 5,486,207 | A | 1/1996 | Mahawili | |
| 5,507,792 | A | 4/1996 | Mason et al. | |
| 5,531,714 | A | 7/1996 | Dahn et al. | |
| 5,531,776 | A | 7/1996 | Ward et al. | |
| 5,624,392 | A | 4/1997 | Saab | |
| 5,634,907 | A | 6/1997 | Rani et al. | |
| 5,643,315 | A * | 7/1997 | Daneshvar | 606/201 |
| 5,676,670 | A | 10/1997 | Kim | |
| 5,701,905 | A | 12/1997 | Esch | |
| 5,709,564 | A | 1/1998 | Yamada et al. | |
| 5,709,654 | A | 1/1998 | Klatz et al. | |
| 5,716,386 | A | 2/1998 | Ward et al. | |
| 5,730,720 | A | 3/1998 | Sites et al. | |
| 5,733,319 | A | 3/1998 | Neilson et al. | |
| 5,737,782 | A | 4/1998 | Matsuura et al. | |
| 5,776,079 | A | 7/1998 | Cope et al. | |
| 5,788,647 | A | 8/1998 | Eggers | |
| 5,837,003 | A | 11/1998 | Ginsburg | |
| 5,862,675 | A | 1/1999 | Scaringe et al. | |
| 5,895,418 | A | 4/1999 | Saringer | |
| 5,908,407 | A | 6/1999 | Frazee et al. | |
| 5,957,963 | A | 9/1999 | Dobak, III | |
| 5,980,561 | A | 11/1999 | Kolen et al. | |
| 6,019,783 | A | 2/2000 | Philips et al. | |
| 6,042,559 | A | 3/2000 | Dobak, III | |
| 6,051,019 | A | 4/2000 | Dobak, III | |
| 6,059,825 | A | 5/2000 | Hobbs et al. | |
| 6,096,068 | A | 8/2000 | Dobak, III et al. | |
| 6,110,139 | A | 8/2000 | Loubser | |
| 6,117,065 | A | 9/2000 | Hastings et al. | |
| 6,117,105 | A | 9/2000 | Bresnaham et al. | |
| 6,124,452 | A | 9/2000 | Di Magno | |
| 6,126,684 | A | 10/2000 | Gobin et al. | |
| 6,146,141 | A | 11/2000 | Schumann | |
| 6,146,411 | A | 11/2000 | Noda et al. | |
| 6,148,634 | A | 11/2000 | Sherwood | |
| 6,149,670 | A | 11/2000 | Worthen et al. | |
| 6,149,677 | A | 11/2000 | Dobak, III | |
| 6,231,594 | B1 | 5/2001 | Dae | |
| 6,283,940 | B1 | 9/2001 | Mulholland | |
| 6,287,326 | B1 * | 9/2001 | Pecor | 607/105 |
| 6,299,599 | B1 | 10/2001 | Pham et al. | |
| 6,338,727 | B1 | 1/2002 | Noda et al. | |
| 6,383,144 | B1 | 5/2002 | Mooney et al. | |
| 6,409,747 | B1 | 6/2002 | Gobin et al. | |
| 6,416,533 | B1 | 7/2002 | Gobin et al. | |
| 6,428,563 | B1 | 8/2002 | Keller | |
| 6,450,990 | B1 | 9/2002 | Walker et al. | |
| 6,464,716 | B1 | 10/2002 | Dobak, III et al. | |
| 6,520,933 | B1 * | 2/2003 | Evans et al. | 604/103.07 |
| 6,527,798 | B2 | 3/2003 | Ginsburg et al. | |
| 6,530,946 | B1 | 3/2003 | Noda et al. | |
| 6,544,282 | B1 | 4/2003 | Dae et al. | |
| 6,551,309 | B1 | 4/2003 | Le Pivert | |
| 6,554,791 | B1 | 4/2003 | Cartledge et al. | |
| 6,589,271 | B1 * | 7/2003 | Tzeng et al. | 607/105 |
| 6,605,106 | B2 | 8/2003 | Schwartz | |
| 6,610,083 | B2 | 8/2003 | Keller et al. | |
| 6,620,131 | B2 * | 9/2003 | Pham et al. | 604/113 |
| 6,620,187 | B2 | 9/2003 | Carson et al. | |
| 6,620,188 | B1 | 9/2003 | Ginsburg et al. | |
| 6,624,679 | B2 | 9/2003 | Tomaivolo et al. | |
| 6,635,079 | B2 | 10/2003 | Unsworth et al. | |
| 6,679,906 | B2 | 1/2004 | Hammack et al. | |
| 6,685,733 | B1 | 2/2004 | Dae et al. | |
| 6,702,840 | B2 * | 3/2004 | Keller et al. | 607/105 |
| 6,706,060 | B2 * | 3/2004 | Tzeng et al. | 607/105 |
| 6,716,188 | B2 | 4/2004 | Noda et al. | |
| 6,719,723 | B2 | 4/2004 | Werneth | |
| 6,719,779 | B2 | 4/2004 | Daoud | |
| 6,726,653 | B2 | 4/2004 | Noda et al. | |
| 6,733,517 | B1 * | 5/2004 | Collins | 607/105 |
| 6,740,109 | B2 | 5/2004 | Dobak, III | |
| 6,749,625 | B2 * | 6/2004 | Pompa et al. | 607/105 |
| 6,796,995 | B2 * | 9/2004 | Pham et al. | 607/105 |
| 6,799,342 | B1 | 10/2004 | Jarmon | |
| 6,843,800 | B1 | 1/2005 | Dobak, III | |
| 6,887,263 | B2 | 5/2005 | Bleam et al. | |
| 6,893,419 | B2 | 5/2005 | Noda et al. | |
| 6,969,399 | B2 | 11/2005 | Schock et al. | |
| 7,001,417 | B2 * | 2/2006 | Elkins | 607/104 |
| 7,001,418 | B2 * | 2/2006 | Noda | 607/105 |
| 7,014,651 | B2 * | 3/2006 | Worthen et al. | 607/105 |
| 7,510,569 | B2 | 3/2009 | Dae et al. | |
| 7,666,215 | B2 | 2/2010 | Callister et al. | |
| 7,822,485 | B2 | 10/2010 | Collins | |
| 7,846,193 | B2 | 12/2010 | Dae et al. | |
| 7,857,781 | B2 | 12/2010 | Noda et al. | |
| 8,105,262 | B2 | 1/2012 | Noda et al. | |
| 8,105,263 | B2 | 1/2012 | Noda et al. | |
| 8,105,264 | B2 | 1/2012 | Noda et al. | |
| 8,109,894 | B2 | 2/2012 | Noda et al. | |
| 2001/0031946 | A1 | 10/2001 | Walker et al. | |
| 2001/0047196 | A1 | 11/2001 | Ginsburg et al. | |
| 2002/0013569 | A1 | 1/2002 | Sterman et al. | |
| 2002/0022823 | A1 | 2/2002 | Luo et al. | |
| 2002/0145525 | A1 | 10/2002 | Friedman et al. | |
| 2002/0183692 | A1 | 12/2002 | Callister | |
| 2002/0198579 | A1 | 12/2002 | Khanna | |
| 2003/0036496 | A1 | 2/2003 | Elsner et al. | |
| 2004/0089058 | A1 | 5/2004 | De Hann et al. | |
| 2004/0102825 | A1 | 5/2004 | Daoud | |
| 2004/0210231 | A1 | 10/2004 | Boucher et al. | |
| 2005/0156744 | A1 | 7/2005 | Pires | |

(56) References Cited

U.S. PATENT DOCUMENTS

| | | | |
|---|---|---|---|
| 2007/0007640 A1 | 1/2007 | Harnden et al. | |
| 2007/0076401 A1 | 4/2007 | Carrez et al. | |
| 2007/0276461 A1 | 11/2007 | Andreas et al. | |
| 2008/0177230 A1* | 7/2008 | Walker et al. | 604/113 |
| 2009/0082857 A1 | 3/2009 | Lashinski et al. | |
| 2010/0228192 A1* | 9/2010 | O'Dea et al. | 604/104 |
| 2013/0090593 A1* | 4/2013 | Dabrowiak | 604/43 |
| 2013/0178923 A1* | 7/2013 | Dabrowiak | 607/105 |

FOREIGN PATENT DOCUMENTS

| | | |
|---|---|---|
| GB | 1183185 | 2/1985 |
| GB | 2212262 | 7/1989 |
| GB | 2383828 | 7/2003 |
| JP | 09-215754 | 8/1997 |
| JP | 10-0127777 | 5/1998 |
| JP | 10-305103 | 11/1998 |
| WO | 9001682 | 2/1990 |
| WO | 9304727 | 3/1993 |
| WO | 9400177 | 1/1994 |
| WO | 9401177 | 1/1994 |
| WO | 9725011 | 7/1997 |
| WO | 9824491 | 6/1998 |
| WO | 9840017 | 9/1998 |
| WO | 0010494 | 3/2000 |
| WO | 0113809 | 3/2001 |
| WO | 0164146 | 9/2001 |
| WO | 0176517 | 10/2001 |
| WO | 0183001 | 11/2001 |

OTHER PUBLICATIONS

F.W. Behmann, E. Bontke, "Intravasale Kühlung", Pffügers Archiv, Bd. 263, S. 145-165 (1956).

Wilhelm Behringer, Stephan Prueckner, Rainer Kenter, Samuel A. Tisherman, Ann Radovsky, Robert Clark, S. William Stezoski, Heremy Henchir, Edwin Klein, Peter Safar, "Rapid Hypothermic Aortic Flush Can Achieve Survival without Brain Damage after 30 Minutes Cardiac Arrest in Dogs", anesthesiology, V. 93, No. 6, Dec. 2000.

Dorraine Day Watts, Arthur Trask, Karen Soeken, Philip Predue, Sheilah Dols, Christopher Kaufman; "Hypothermic Coagulopathy in trauma: Effect of Varying levels of Hypothermia on Enzyme Speed, Platelet Function, and Fibrinolytic Activity". The Journal of Trauma: Injury, Infection, and Critical Care, Vo. 44, No. 5 (1998).

* cited by examiner

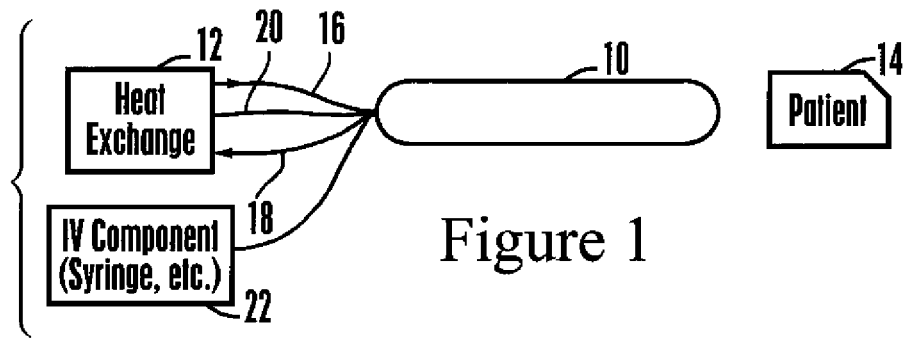
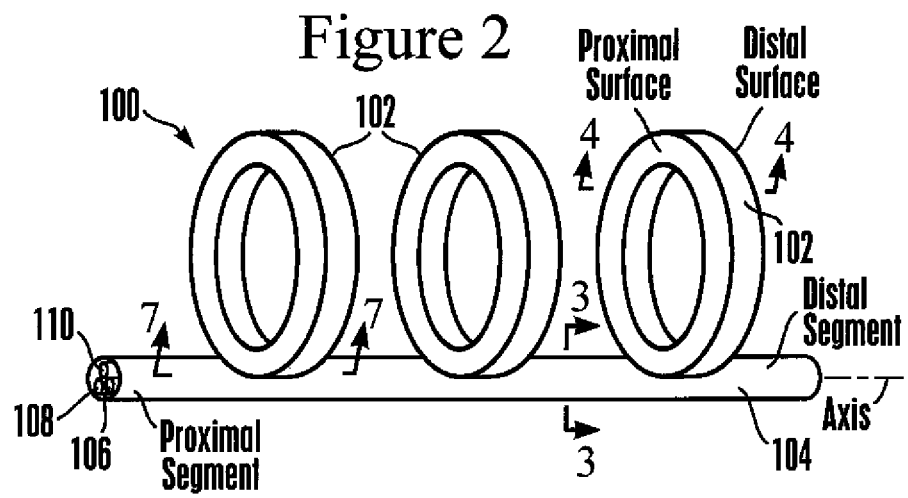
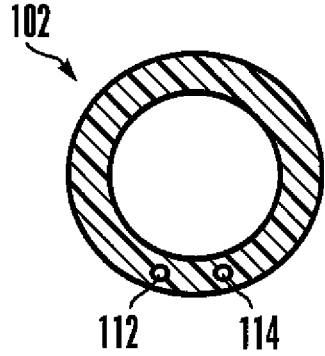 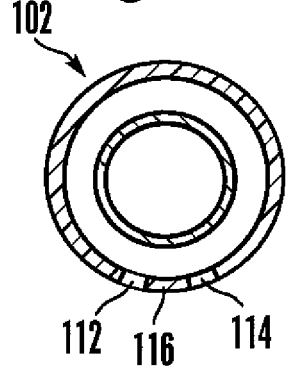 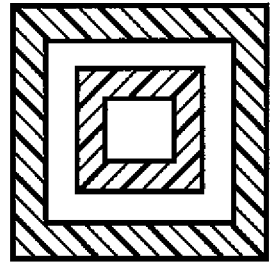

US 9,241,827 B2

INTRAVASCULAR HEAT EXCHANGE CATHETER WITH MULTIPLE SPACED APART DISCRETE COOLANT LOOPS

FIELD OF THE INVENTION

The present application relates generally to patient temperature control systems.

BACKGROUND OF THE INVENTION

It has been discovered that the medical outcome for a patient suffering from severe brain trauma or from ischemia caused by stroke or heart attack or cardiac arrest is improved if the patient is cooled below normal body temperature (37° C.). Furthermore, it is also accepted that for such patients, it is important to prevent hyperthermia (fever) even if it is decided not to induce hypothermia. Moreover, in certain applications such as post-CABG surgery, skin graft surgery, and the like, it might be desirable to rewarm a hypothermic patient.

As recognized by the present application, the above-mentioned advantages in regulating temperature can be realized by cooling or heating the patient's entire body using a closed loop heat exchange catheter placed in the patient's venous system and circulating a working fluid such as saline through the catheter, heating or cooling the working fluid as appropriate in an external heat exchanger that is connected to the catheter. The following U.S. patents, all of which are incorporated herein by reference, disclose various intravascular catheters/systems/methods for such purposes: U.S. Pat. Nos. 6,881,551 and 6,585,692 (tri-lobe catheter), U.S. Pat. Nos. 6,551,349 and 6,554,797 (metal catheter with bellows), U.S. Pat. Nos. 6,749,625 and 6,796,995 (catheters with non-straight, non-helical heat exchange elements), U.S. Pat. Nos. 6,126,684, 6,299,599, 6,368,304, and 6,338,727 (catheters with multiple heat exchange balloons), U.S. Pat. Nos. 6,146,411, 6,019,783, 6,581,403, 7,287,398, and 5,837,003 (heat exchange systems for catheter), U.S. Pat. No. 7,857,781 (various heat exchange catheters).

SUMMARY OF THE INVENTION

The details of the present invention, both as to its structure and operation, can best be understood in reference to the accompanying drawings, in which like reference numerals refer to like parts, and in which:

A catheter includes a proximal segment having a supply lumen configured to receive working fluid from a heat exchange system and a return lumen configured to return working fluid to the heat exchange system. The catheter also includes a distal segment in fluid communication with the proximal segment and defining plural spaced apart discrete loops, each communicating with the supply lumen and each being connected to an adjacent loop by a substantially straight connector segment.

The loops when inflated with working fluid can be toroidal-shaped, disk-shaped, rectangular-shaped or triangular-shaped. Each loop can define a proximal surface and a distal surface parallel to the proximal surface and oriented transversely to a long axis of the return tube. The distal-most loop can be connected to the return lumen.

Each individual loop may include a supply port communicating with the supply lumen and a fluid channel defined by the loop and a return port communicating with the supply lumen and with the fluid channel of the loop, such that working fluid can circulate through the fluid channel from the supply port to the return port. The ports can be closely juxtaposed with each other and straddle a separator such that working fluid must flow from the supply port substantially completely through the fluid channel to the return port.

In an aspect, a catheter includes a series of hollow loops arranged along a tube for carrying working fluid from a heat exchange system to exchange heat with a patient in whom the catheter is advanced. When inflated, the loops are oriented transverse to a long axis of the catheter throughout their respective outer peripheries and are parallel to each other. The loops circumscribe a hollow passageway through which blood can flow. The loops are configured such that blood can also flow around the outer peripheries of the loops.

In an aspect, a method includes providing a heat exchange catheter with a supply lumen configured for receiving working fluid from a heat exchange system and a return lumen configured for returning working fluid to the heat exchange system. The method also includes providing plural discrete loops on the catheter receiving working fluid from the supply lumen and circulating returning working fluid through the loop. The loops are spaced from each other and connected to each other only by a flexible tube.

BRIEF DESCRIPTION OF THE DRAWINGS

FIG. 1 is a schematic diagram showing an example catheter engaged with an example heat exchange system;

FIG. 2 is a perspective view of the heat exchange region showing as an example three spaced apart loops on a catheter with a supply and a return lumen and a single infusion lumen for simplicity, it being understood that additional infusion lumens may be provided;

FIG. 3 is a transverse view of a loop showing the supply and return ports that communicate with the supply and return lumens, respectively of the catheter;

FIG. 4 is a transverse cross-section as seen along the line 4-4 in FIG. 2;

FIG. 5 is a transverse cross-section of an alternate rectangular embodiment as would be seen along the line 4-4 in FIG. 2;

DETAILED DESCRIPTION OF THE PREFERRED EMBODIMENT

Referring initially to FIG. 1, an intravascular temperature management catheter 10 is in fluid communication with a catheter temperature control system 12 that includes a processor executing logic that in some non-limiting examples is in accordance with disclosure in the above-referenced system patents to control the temperature of working fluid circulating through the catheter 10 in accordance with a treatment paradigm responsive to patient core temperature feedback signals. In accordance with present principles, the catheter 10 can be used to induce therapeutic hypothermia in a patient 14 using the catheter, in which coolant such as but not limited to saline circulates in a closed loop, such that no coolant enters the body. Such treatment may be indicated for stroke, cardiac arrest (post-resuscitation), acute myocardial infarction, spinal injury, and traumatic brain injury. The catheter 10 can also be used to warm a patient, e.g., after bypass surgery or burn treatment, and to combat hyperthermia in, e.g., patient suffering from sub-arachnoid hemorrhage or intracerebral hemorrhage.

As shown, working fluid such a refrigerant may be circulated between the heat exchange system 12 and catheter 10 through supply and return lines 16, 18 that connect to the proximal end of the catheter 10 as shown. Note that as used herein, "proximal" and "distal" in reference to the catheter are relative to the system 12. A patient temperature signal from a catheter-borne temperature sensor may be provided to the system 12 through an electrical line 20 or wirelessly if desired. Alternatively, a patient temperature signal may be provided to the system 12 from a separate esophageal probe or rectal probe or tympanic sensor or bladder probe or other temperature probe that measures the temperature of the patient 14.

The catheter 10, in addition to interior supply and return lumens through which the working fluid is circulated, may also have one or more infusion lumens connectable to an IV component 22 such as a syringe or IV bag for infusing medicaments into the patient, or an instrument such as an oxygen or pressure monitor for monitoring patient parameters, etc.

The catheter 10 can be positioned typically in the vasculature of the patient 14 and more preferably in the venous system of the patient 14 such as in the inferior vena cava through a groin insertion point or the superior vena cava through a neck (jugular or subclavian) insertion point.

Figure 6:
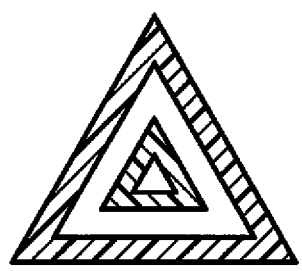
FIG. 6 is a transverse cross-section of an alternate triangular embodiment as would be seen along the line 4-4 in FIG. 2.

Now referring to FIGS. 2-4, a first embodiment of the catheter 10, generally designated 100, is shown with a plurality of spaced-apart hollow coolant loops 102 that may be made of medical grade balloon material. While the loops 102 are shown in a disk-shape configuration when inflated with working fluid, in other embodiments the loops 102 may be toroidal-shaped when inflated. In both cases, the loops have the ring-shaped circular transverse cross-sections shown in FIGS. 3 and 4. Or, the loops may be made to assume an ovular cross-section when inflated. In other embodiments and briefly referring to FIGS. 5 and 6, the loops may assume non-round transverse shapes when inflated, e.g., rectangular (FIG. 5), triangular (FIG. 6), or other shapes.

Returning to FIGS. 2 and 3, a series of coolant loops 102 and a flexible connector segment 104 is shown. The flexible connector segment 104 includes a supply lumen 106 and a return lumen 108 and is attached to each loop 102 at the base of each loop 102. Each loop 102 may be continuously molded to the connector segment 104 or may be attached to the connector segment 104 by means of an adhesive. Additional lumens, such as but not limited to an infusion lumen 110 connected to an IV component 22 such as a syringe or IV bag for infusing medicaments into the patient, or an instrument such as an oxygen or pressure monitor for monitoring patient parameters, etc., may be included as part of the connector segment 104. The fluid of the infusion lumen 110 is isolated from the working fluid in the supply lumen 106 and the return lumen 108 and may enter the patient 14 through an open distal end of the catheter 100.

In the embodiment shown, each loop 102 defines a proximal surface and a distal surface parallel to the proximal surface and oriented transversely to a long axis of the return tube 108. The loop 102 in FIG. 3, illustrated from a proximal perspective, forms a ring with a supply port 112 on the proximal side of the base of the loop 102 and a return port 114 on the distal side of the base of the loop 102. The working fluid in the proximal supply lumen 106 enters the loop 102 through the supply port 112 and then re-enters the supply lumen 106 through the return port 114. The illustration of a loop 102 in FIG. 4 includes a separator 116 situated between the supply port 112 and return port 114.

Figure 7:
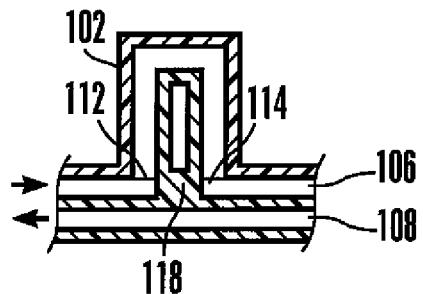
FIG. 7 is a cross-section as would be seen along the 7-7 in FIG. 2 of an alternate embodiment in which the supply and return ports of a loop are slightly offset axially.

In this embodiment, all but the distal-most loop receives working fluid from the supply lumen 106 on one side of the supply lumen 106 and returns it to the supply lumen 106 on the opposite side of the supply lumen 106, with the supply lumen 106 being provided with a divider 118 between the two sides to ensure that working fluid flows from the supply lumen 106, into the supply port 112 of the loop 102, around the loop 102, out of the return port 114, and back into the supply lumen 106. The distal-most loops has a return port 114 connected to a return lumen 108, which conveys the working fluid proximally back through the catheter 100 to the heat exchange system 12. In other embodiments, instead of being radially offset, the supply port 112 and return port 114 of a loop 102 may be slightly axially staggered as shown in FIG. 7 such that the divider 118 in the supply lumen 106 of the catheter 100 extends axially a short way through the supply lumen 106 as shown in FIG. 7. In such an embodiment, the distal and proximal surfaces of the loop 102 will remain generally parallel to each other but may be angled slightly from being absolutely transverse to the long axis of the catheter 100 owing to axial offset of the supply port 112 and return port 114.

Note that each loop 102 in the example shown thus receives coolant from the supply lumen 106 and returns it to the supply lumen 106, except the distal-most loop, whose return port is connected to the return lumen 108. Note that in addition to the separator 116 within each loop 102 to separate the supply port 112 from the return port 114, there is also the blockage 118 in the catheter supply lumen 106 to ensure all coolant in the supply lumen 106 flows through the first loop, back into the supply lumen 106 to the next loop, through the second loop, and so on. Also note that the flow can be reversed, i.e., the distal most loop can receive working fluid first before all other loops through an elongated straight supply lumen, with the working fluid then being fed back through the other loops in a proximal direction. In the first case all loops 102 get fed from the supply lumen 106 and the last loop feeds it back to the return lumen 108; in the second case the distal loop gets fed from the supply lumen 106, feeding back the fluid through the return lumen 108 through each subsequent loop in sequence from distal to proximal.

Figure 8:
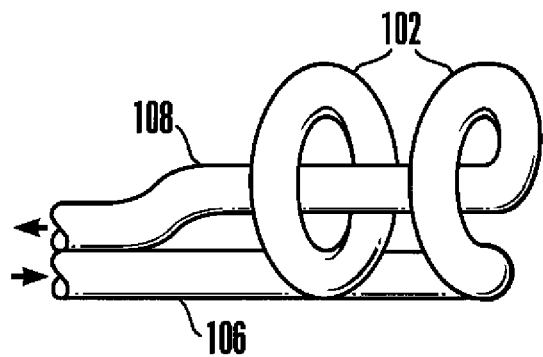
FIG. 8 shows an alternate embodiment of the distal portion of an alternate embodiment in which the return lumen is distanced from the supply lumen except at the proximal-most portion of the catheter to reduce heat exchange between the lumens.

In the embodiment of the catheter 100 shown in FIG. 8, the distal-most loop 102 does not form a complete ring. Rather, the distal-most loop 102 forms a half-ring and connects to the return lumen 108, which then extends in a proximal direction through the other loops 102. The working fluid in the supply lumen 106 flows through the loops 102 and back into the supply lumen 106 in a distal-direction until the distal-most loop 102, at which point the working fluid enters the return lumen 108 and flows in a proximal direction back to the heat exchange system 12. The supply lumen 106 and return lumen 108 in this embodiment are spaced from each other in order to achieve a decreased amount of heat exchange between elements of the catheter 100 and increased heat exchange between the catheter 100 and the patient 14.

While the particular INTRAVASCULAR HEAT EXCHANGE CATHETER WITH MULTIPLE SPACED APART DISCRETE COOLANT LOOPS is herein shown and described in detail, it is to be understood that the subject matter which is encompassed by the present invention is limited only by the claims.

What is claimed is:

1. A catheter, comprising:
   a proximal segment having a supply lumen configured to receive working fluid from a heat exchange system and a return lumen configured to return the working fluid to the heat exchange system; and
   a distal segment in fluid communication with the proximal segment and defining plural spaced apart discrete loops, each of the plural spaced apart discrete loops communicating with the supply lumen and each being connected to an adjacent loop of the plural spaced apart discrete loops by a connector segment, each loop of the plural spaced apart discrete loops having, when inflated, a wall enclosing a respective lumen through which the working fluid can flow and a central opening formed by the wall through which fluid external to the catheter can flow, the plural spaced apart discrete loops being connected together by a single shaft, wherein at least some of the loops when inflated are toroidal-shaped or disk-shaped, wherein each loop of the plural spaced apart discrete loops defines a proximal surface and a distal surface parallel to the proximal surface and oriented perpendicular to a long axis of the shaft.

2. The catheter of claim 1, wherein the plural spaced apart discrete loops when inflated are toroidal-shaped.

3. The catheter of claim 1, wherein the plural spaced apart discrete loops when inflated are disk-shaped.

4. A catheter, comprising:
   a proximal segment having a supply lumen configured to receive working fluid from a heat exchange system and a return lumen configured to return the working fluid to the heat exchange system; and
   a distal segment in fluid communication with the proximal segment and defining plural spaced apart discrete loops, each of the plural spaced apart discrete loops communicating with the supply lumen and each of the plural spaced apart discrete loops being connected to an adjacent loop by a connector segment, each of the plural spaced apart discrete loops having, when inflated, a wall enclosing a respective lumen through which the working fluid can flow and a central opening formed by the wall through which fluid external to the catheter can flow, the loops of the plural spaced apart discrete loops being connected together by a single shaft,
   wherein the loops when inflated with working fluid are rectangular-shaped.

5. The catheter of claim 1, wherein at least one loop of the plural spaced apart discrete loops includes a supply port communicating with the supply lumen and a fluid channel defined by the at least one loop of the plural spaced apart discrete loops and a return port communicating with the return lumen and with the fluid channel, such that the working fluid circulates through the fluid channel from the supply port to the return port.

6. The catheter of claim 5, wherein the supply and return ports are proximate to each other and straddle a separator such that the working fluid must flow from the supply port substantially completely through the fluid channel to the return port.

7. The catheter of claim 1, wherein each loop of the plural spaced apart discrete loops is connected to a return tube communicating with the return lumen of the proximal segment.

8. A catheter comprising:
   loops arranged along a tube for carrying working fluid from a heat exchange system, wherein the loops, when inflated, are oriented perpendicular to a long axis of the catheter throughout respective closed outer peripheries, and are oriented parallel to each other, and circumscribe a hollow passageway through which blood can flow, the loops being configured such that blood also can flow around the closed outer peripheries of the loops, the loops receiving the working fluid from a supply lumen of a shaft, the supply lumen extending from a proximal segment of the shaft to a supply port of a first one of the loops located most proximally and then again between a return port of the first loop to a supply port of second one of the loops that is located more distally than the first loop, wherein at least some of the loops when inflated are toroidal-shaped or disk-shaped.

9. The catheter of claim 8, wherein the loops when inflated are toroidal-shaped.

10. The catheter of claim 8, wherein the loops when inflated are disk-shaped.

11. A catheter comprising:
    loops arranged along a tube for carrying working fluid from a heat exchange system, wherein the loops when inflated are oriented transverse to a long axis of the catheter throughout respective closed outer peripheries, and are oriented parallel to each other, and circumscribe a hollow passageway through which blood can flow, the loops being configured such that blood also can flow around the outer peripheries of the loops, the loops receiving the working fluid from a supply lumen of a shaft, the supply lumen extending from a proximal segment of the shaft to a supply port of a first loop located most proximally and then again between a return port of the first loop to a supply port of second loop located more distally than the first loop,
    wherein the loops when inflated are rectangular-shaped.

12. The catheter of claim 8, wherein each loop includes a supply port communicating with a supply lumen defined by the catheter and a fluid channel defined by the loop and a return port communicating with the fluid channel, such that the working fluid circulates through the fluid channel from the supply port to the return port.

13. The catheter of claim 12, wherein the supply and return ports are proximate to each other and straddle a separator such that the working fluid must flow from the supply port substantially completely through the fluid channel to the return port.

14. The catheter of claim 8, wherein each loop is connected to a return tube communicating with a return lumen of a proximal segment.

15. The catheter of claim 14, wherein each loop defines a proximal surface and a distal surface parallel to the proximal surface and oriented transversely to a long axis of the return tube.

16. A device comprising:
    a shaft with a straight supply lumen configured for fluid communication with a heat exchange system and a straight return lumen configured for communicating with the heat exchange system; and
    loops coupled to the shaft and fluidly communicating with the supply lumen with a fluid communication path being defined through the loops, the loops being spaced from each other along a longitudinal dimension defined by the shaft, each loop having a wall enclosing a respective lumen and a central opening formed by the wall through which fluid external to the catheter can flow, wherein each loop is formed with a respective supply port and a respective return port communicating with the respective lumen of the loop, each loop configured for fluidly communicating with the supply lumen and for fluidly communicating with the return lumen, the supply port being separated from the respective return port, each loop being physically connected to an adjacent loop by at least one of: the straight supply lumen, the straight return lumen.

* * * * *